United States Patent [19]

Iwao et al.

[11] 4,070,169

[45] Jan. 24, 1978

[54] CHROMATOGRAPHIC COLUMN OVEN

[75] Inventors: Kumiy Roy Iwao, Lafayette; Fritz Hunt Henshaw, Danville, both of Calif.

[73] Assignee: Varian Associates, Inc., Palo Alto, Calif.

[21] Appl. No.: 772,612

[22] Filed: Feb. 28, 1977

[51] Int. Cl.² .............................................. B01D 15/08
[52] U.S. Cl. ........................................ 55/267; 55/386
[58] Field of Search .................... 55/67, 197, 386, 208, 55/267

[56] References Cited

U.S. PATENT DOCUMENTS

| | | | |
|---|---|---|---|
| 3,165,147 | 1/1965 | Roof et al. | 55/386 X |
| 3,305,000 | 2/1967 | Bullen et al. | 55/386 X |
| 3,385,099 | 5/1968 | Diem et al. | 73/23.1 |
| 3,422,604 | 1/1969 | Haase | 55/386 |

*Primary Examiner*—John Adee

*Attorney, Agent, or Firm*—Stanley Z. Cole; Gerald M. Fisher; John J. Morrissey

[57] ABSTRACT

In a chromatographic column oven, a particular arrangement of a fan, heater and baffles provides low thermal gradients and rapid oven cool-down. Low thermal gradients are obtained by providing an air circulation pattern that promotes optimum mixing of the air within the oven enclosure. A fast cool-down time is obtained by providing a high-velocity air flow along the walls of the oven enclosure. A fan is mounted substantially at the geometric center of a first wall of the oven enclosure. A second wall of the enclosure, which faces the first wall, comprises a door for providing access to the oven enclosure. An elongate heating element is mounted on the first wall so as to substantially surround the periphery of the fan. A plurality of baffles are mounted symmetrically around the periphery of the fan on and extending perpendicularly from the first wall. A gap is provided between each particular baffle and the wall or walls intersecting the first wall nearest that particular baffle.

4 Claims, 2 Drawing Figures

U.S. Patent  Jan. 24, 1978  4,070,169
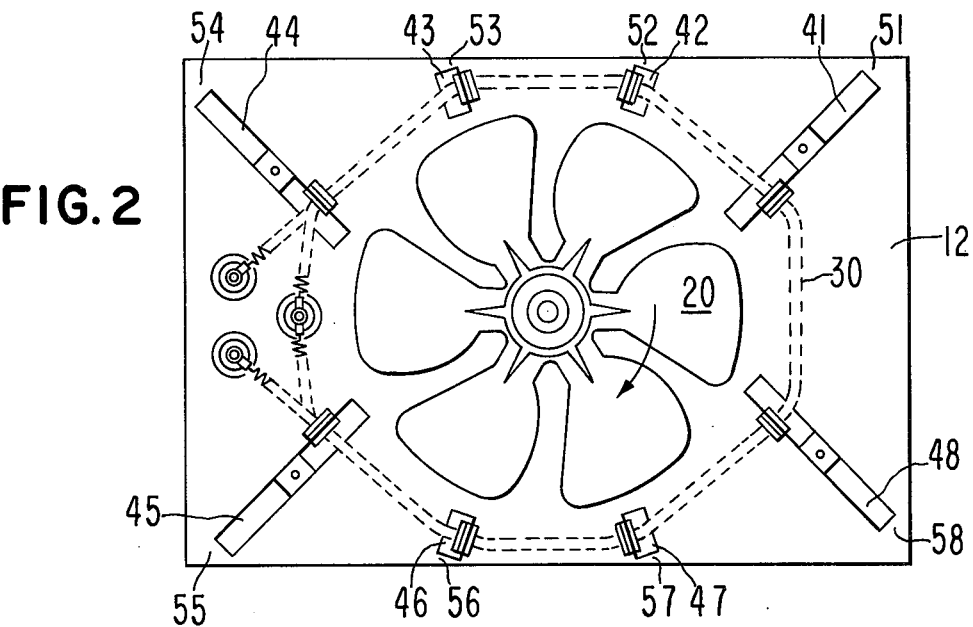
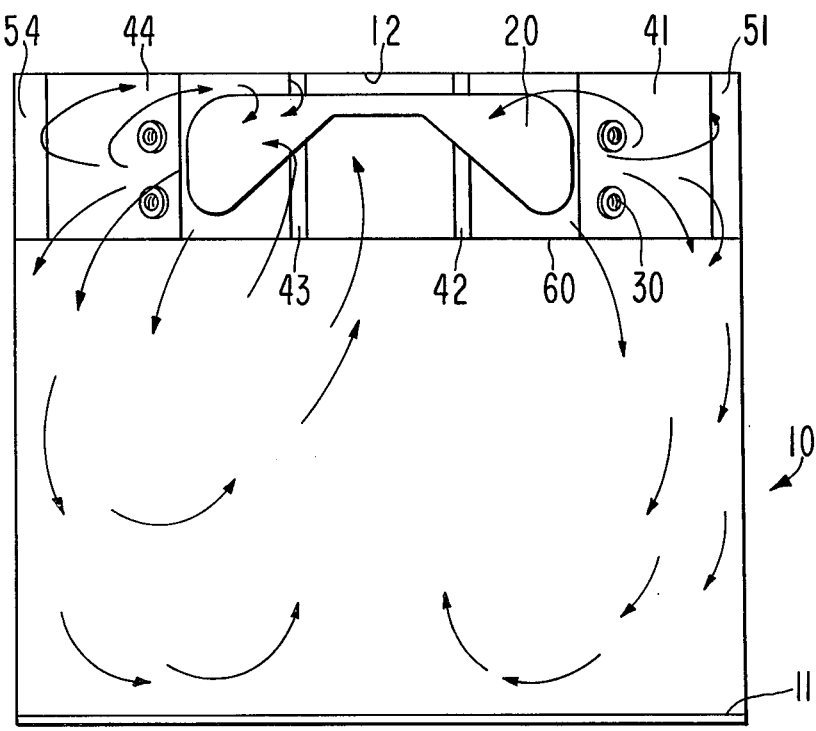

CHROMATOGRAPHIC COLUMN OVEN

BACKGROUND OF THE INVENTION

In operation, chromatographic columns are controllably heated in oven enclosures. It is desirable to maintain an air circulation pattern within such an oven enclosure that will prevent high thermal gradients from occurring. It is also desirable to provide a rapid oven cool-down time when the oven door is opened, so as to facilitate accessibility to the chromatographic column or columns mounted within the oven enclosure.

In the prior art, air circulation within the oven enclosure has been accomplished with various arrangements of fans or blowers, baffles, and heater elements. Typically, in the prior art, air has been allowed to come off the tips of the blades of a fan or blower, and then to pass over a heater element or elements. The air, after having been thus heated, was then directed over the chromatographic column (or columns) to the oven walls, whereupon the air would be directed to return to the central portion of the fan or blower. At the fan or blower, the air would pass along the blades and subsequently leave the tips of the blades to repeat the circulation cycle. In U.S. Pat. No. 3,422,603, a toroidal circulation pattern is described, wherein air is drawn into an impeller in an axial direction, and is discharged toward the walls of the oven in a direction substantially at right angles to the axis of the impeller.

With the air circulation patterns provided by arrangements known to the prior art, only a fraction of the air leaving the tips of the fan blades actually passes over the heater element or elements. In those prior art arrangements wherein the fans or blowers are not symmetrically disposed within the oven enclosure, uneven air-flow patterns are generated which increase the thermal gradients within the oven enclosure. With prior art oven enclosures of cubical or right-parallelepiped configurations, even with symmetrically disposed fans or blowers, the air circulation patterns cause high-velocity air flow at the corners and relatively low-velocity air flow away from the corners. Such uneven air-flow distributions likewise tend to increase the thermal gradients within the oven enclosures.

SUMMARY OF THE INVENTION

It is an object of this invention to provide an air circulation pattern within a chromatographic column oven enclosure that results in low thermal gradients in the enclosure and a rapid oven cool-down capability.

It is a particular object of this invention to obtain an air circulation pattern within a chromatographic column oven enclosure that provides a high-velocity air flow along the walls of the enclosure.

It is also a particular object of this invention to obtain an air circulation pattern within a chromatographic column oven enclosure by using an arrangement of a fan, heater and baffles that maximizes the quantity of air leaving the tips of the fan blades and passing over a heater, whereby thermal gradients within the oven enclosure can be minimized.

It is also a particular object of this invention to provide an air circulation pattern within a chromatographic column oven enclosure by using an arrangement of a fan, heater and baffles that causes a significant quantity of air to pass in the vicinity of the heater on returning to the fan, whereby thermal gradients within the oven enclosure can be minimized.

Another object of this invention is to provide an arrangement of a fan, heater and baffles within a chromatographic column oven enclosure such that a high heat transfer coefficient can be maintained along the wall of the enclosure furthest away from the oven door, thereby providing rapid oven cool-down when the oven door is opened.

A further object of this invention is to provide an arrangement of a fan, heater and baffles within a chromatographic column oven enclosure such as to maintain an even flow distribution within the enclosure by equalizing the fan head pressure between the baffles.

In a particular embodiment of this invention, a fan is mounted at substantially the geometric center of a first wall of the oven enclosure. A second wall of the oven enclosure, which faces the first wall, comprises a door for providing access to the interior of the enclosure. A chromatographic column or plurality of columns can be mounted within the enclosure. An elongate heating element is mounted on the first wall in a configuration that substantially surrounds the periphery of the fan. A plurality of baffles are likewise mounted on the first wall, the baffles being symmetrically disposed with respect to each other and with respect to the fan. The baffles are preferably of planar configuration, and extend perpendicularly from the plane of the first wall. A gap is provided between each baffle and the nearest wall or walls that intersect the wall to which the baffle is attached. In the preferred embodiment, the oven enclosure is of right-parallelepiped configuration, and there are at least four baffles, one baffle being disposed adjacent each corner of the first (i.e., rear) wall of the enclosure. A description of the particular oven configuration contemplated for the preferred embodiment of this invention is disclosed in copending U.S. patent application Nos. 662,767 and 662,769.

DESCRIPTION OF THE DRAWINGS

FIG. 1 shows a plan view of a chromatographic column oven enclosure, with a fan, heater and baffles mounted on one wall thereof according to this invention.

FIG. 2 shows a front view of the wall in FIG. 1 upon which the fan, heater and baffles are mounted.

DESCRIPTION OF A PREFERRED EMBODIMENT

A chromatographic column oven 10 is illustrated in FIG. 1 wherein a generally right-parallelepiped volume is enclosed by rectangular walls. A front wall 11 comprises a door for providing access to the interior volume of the oven 10. A back wall 12 faces the front wall (i.e., door) 11. Mounted on the back wall 12 are a fan 20, an elongate heater element 30, and a plurality of baffles indicated in FIG. 1 by the reference numbers 41, 42, 43 and 44.

The back wall 12 is shown in frontal view in FIG. 2. The fan 20 is mounted at substantially the geometric center of the wall 12, and the heater element 30 is mounted to surround the periphery of the fan 20. In the embodiment shown, there are eight baffles, indicated by the reference numbers 41, 42, 43, 44, 45, 46, 47 and 48, which are mounted symmetrically with respect to each other around the periphery of the fan 20.

For a rectangular oven wall 12, as shown in the preferred embodiment, the corner baffles 41, 44, 45 and 48 are deemed essential. Other baffles, such as the baffles 42, 43, 46 and 47, are provided to further reduce thermal gradients within the oven enclosure. In general, the reduction of thermal gradients within the interior volume of the oven 10 increases with the number of baffles provided. An upper practical limit on the number of baffles is determined by the size of the fan 20 in relation to the size of the wall 12.

The baffles are preferably of planar configuration, and extend perpendicularly away from the wall 12. An airgap is provided between each baffle and the nearest side walls running perpendicular to wall 12. These airgaps are indicated in FIG. 2 by the reference numbers 51, 52, 53, 54, 55, 56, 57 and 58, respectively.

A perforated screen structure 60 may be positioned parallel to the rear wall 12 and forward of the fan, heater and baffles. Such a screen 60 serves to prevent an operator's fingers or tools from coming into contact with the fan, heater or baffles during arrangement or adjustment of chromatographic columns within the oven enclosure.

It has been found that the arrangement of the fan, heater and baffles described above provides lower thermal gradients witin the oven enclosure and more rapid cool-down time then was possible with any arrangement known to the prior art. With the arrangement of this invention, each baffle controls the air coming off the blades of the fan 20. The air flow gaps 51, 52, 53, 54, 55, 56, 57 and 58 provide a means for equalizing the fan head pressure between the baffles, thus eliminating abrupt changes in the air-flow direction within the oven enclosure.

It has also been found that the arrangement described above provides a high-velocity air flow near the walls of the oven enclosure. This feature provides a higher heat transfer coefficient along the rear wall 12 than was possible with any arrangement known to the prior art. Consequently, a more rapid oven cool-down time can be obtained with the present arrangement.

It has also been found that the arrangement described above causes an air circulation pattern within the oven enclosure whereby a significant portion of the air is heated as it returns to the fan. With prior art arrangements, air was usually heated only upon exiting from the tips of the fan blades. Consequently, the present arrangement facilitates mixing of the air within the oven enclosure, thereby serving to minimize thermal gradients within the enclosure.

This invention has been described herein in terms of a particular geometrical configuration for the oven enclosure, and in terms of a particular disposition of the baffles. It is recognized that other oven configurations, and other dispositions of the baffles, are possible without departing from the scope of this invention. Therefore, the above description is to be considered as illustrative and not as limiting. The invention is limited only by the following claims.

What is claimed is:

1. A chromatographic column oven comprising walls to enclose an interior oven volume, a fan mounted at substantially the geometric center of a first one of said walls, a second one of said walls facing toward said first wall, said second wall comprising a door for providing access to said interior oven volume, an elongate heating element mounted on said first wall, said heating element substantially surrounding the periphery of said fan, a plurality of baffles mounted on said first wall, said baffles extending generally perpendicularly from said first wall and being symmetrically disposed around the periphery of said fan.

2. The chromatographic column oven of claim 1 wherein said interior oven volume is formed by the intersection of a plurality of said walls with said first wall, and wherein each of said baffles is spaced apart from the walls intersecting said first wall.

3. The chromatographic column oven of claim 1 wherein said baffles are of generally planar configuration.

4. The chromatographic column oven of claim 1 wherein said first wall is generally rectangular, and wherein one of said baffles is disposed adjacent each corner of said first wall.

* * * * *